United States Patent [19]
Quistgaard

[11] Patent Number: 5,860,924
[45] Date of Patent: Jan. 19, 1999

[54] THREE DIMENSIONAL ULTRASONIC DIAGNOSTIC IMAGE RENDERING FROM TISSUE AND FLOW IMAGES

[75] Inventor: Jens Ulrich Quistgaard, Seattle, Wash.

[73] Assignee: Advanced Technology Laboratories, Inc., Bothell, Wash.

[21] Appl. No.: 756,853

[22] Filed: Nov. 26, 1996

[51] Int. Cl.[6] ........................................... A61B 8/06
[52] U.S. Cl. .......................................... 600/441; 128/916
[58] Field of Search ........................ 128/660.07, 661.01, 128/916, 660.05; 600/441, 443, 447

[56] References Cited

U.S. PATENT DOCUMENTS

| | | | |
|---|---|---|---|
| 4,694,434 | 9/1987 | von Ramm et al. | 367/7 |
| 4,794,932 | 1/1989 | Baba | 128/661.09 |
| 5,282,471 | 2/1994 | Sato | 128/660.07 |
| 5,295,486 | 3/1994 | Wollschlager et al. | 128/661.01 |
| 5,329,929 | 7/1994 | Sato | 128/660.65 |
| 5,396,890 | 3/1995 | Weng | 128/660.07 |
| 5,474,073 | 12/1995 | Schwartz et al. | 128/916 X |
| 5,485,842 | 1/1996 | Quistgaard | 128/66.07 |
| 5,501,223 | 3/1996 | Washburn et al. | 128/661.09 |

OTHER PUBLICATIONS

Three–Dimensional Reconstruction of Echocardiograms Based on Orthogonal Sections, S. Tamura et al., Pattern Recog., (1985) p. 115.

Multidimensional Ultrasonic Imaging for Cardiology, H.A. McCann et al. Proc. IEEE, v. 76, No. 9, (Sep. 1988) pp. 1063–1073.

VoxelView 2.5 User Guide, Vital Images, Inc. (1995), introduction, Chapter 7 & Chapter 10.

V–Buffer: Visible vol. Rendering, by C. Upson et al. in Computer Graphics, vol. 22, No. 4 (Aug. 1988) at pp. 59–64.

Primary Examiner—Francis Jaworski
Attorney, Agent, or Firm—W. Brinton Yorks, Jr.

[57] ABSTRACT

A medical diagnostic ultrasound system is described in which ultrasonic B mode tissue information and Doppler flow information is acquired from a volumetric region of the body and processed in an interleaved sequence to render a three dimensional image. The three dimensional rendering processes the B mode and Doppler flow information to give priority to tissue information, flow information, or a blend of the two.

10 Claims, 4 Drawing Sheets

THREE DIMENSIONAL ULTRASONIC DIAGNOSTIC IMAGE RENDERING FROM TISSUE AND FLOW IMAGES

This invention relates to medical ultrasonic diagnostic imaging techniques and, in particular, to three dimensional rendering of ultrasonic tissue and flow images.

U.S. patent [application Ser. No. 08/638,710, filed Apr. 29, 1996] describes an ultrasound system which produces composite renderings of three dimensional ultrasonic images of both tissue and vasculature. In the prior art, such as described in U.S. Pat. Nos. 5,329,929 and 5,295,486, precise three dimensional renderings are produced from image data stored in a three dimensional memory. When image data of a three dimensional (3D) volume is arranged in a three dimensional memory, it can be manipulated freely while retaining the three dimensional orientation of each data point, as each data point has a unique 3D x,y,z address. Moreover, two such volumetric data sets can be spatially related to each other, due to the retention of 3D addresses by each data point in each data set. However, in order for the 3D data to be organized into a three dimensional memory, each data point must be encoded with a 3D address at the time of acquisition, which generally must be done by complex, cumbersome mechanisms which record the x, y, and z addresses of the data. Such devices are disdained by physicians, who enjoy the speed, agility and ease of use of conventional two dimensional (2D) imaging probes. Moreover, ultrasound system architectures are generally designed to store images in 2D image frame storage devices, not three dimensional memories.

In order to easily adapt a conventional ultrasound system architecture for 3D image rendering, and to use conventional planar imaging probes, it is desirable be able to operate upon 2D image frames without the need for a three dimensional memory. An improvement over the three dimensional memory is a "z-buffer" for 2D image memories, which records and tracks the position of each 2D image in the third, or z dimension. The z-buffer is consulted whenever the z dimension of a pixel is needed, such as when deciding whether a pixel of one 2D image is spatially located in front of or behind the pixel of another 2D image. However, the use of a z-buffer imposes additional complexity on conventional 2D ultrasound system architecture, as the z-buffer must be created, its accuracy continually maintained, and continually referred to when operating on 2D image frames for three dimensional processing.

Thus, it is desirable to be able to render three dimensional images in an ultrasound system without the need for a three dimensional memory or a z-buffer. Furthermore, it is particularly desirable to be able to render composite 3D images of tissue and bloodflow, as described in the aforementioned U.S. patent [application Ser. No. 08/638,710], without the need for either a three dimensional memory or a z-buffer.

In accordance with the principles of the present invention, a technique is provided for producing three dimensional ultrasonic presentations of both tissue and blood flow (or motion) without the need for a three dimensional memory or z-buffer. A set of two dimensional frames of ultrasonic tissue data and a set of two dimensional frames of ultrasonic flow or motion data are acquired from a common volumetric region of the body. The data sets are acquired in close time proximity so as to maintain the spatial correspondence of sequential frames of the two data sets. An ultrasonic imaging system includes means for rendering a three dimensional presentation of the combined tissue and flow data sets through interleaved processing of tissue and flow frames in sequence. Such interleaved processing retains the relative spatial correspondence of the data of the two dimensional frames during the rendering operation, resulting in a perceptionally accurate 3D image presentation, in which tissue and vessels which pass behind and in front of other tissue and vessels as the 3D view changes are properly spatially depicted. Thus, three dimensional renderings of tissue and flow can be formed in a manner which is fully compatible with existing two dimensional ultrasound system architectures.

Figure 1:
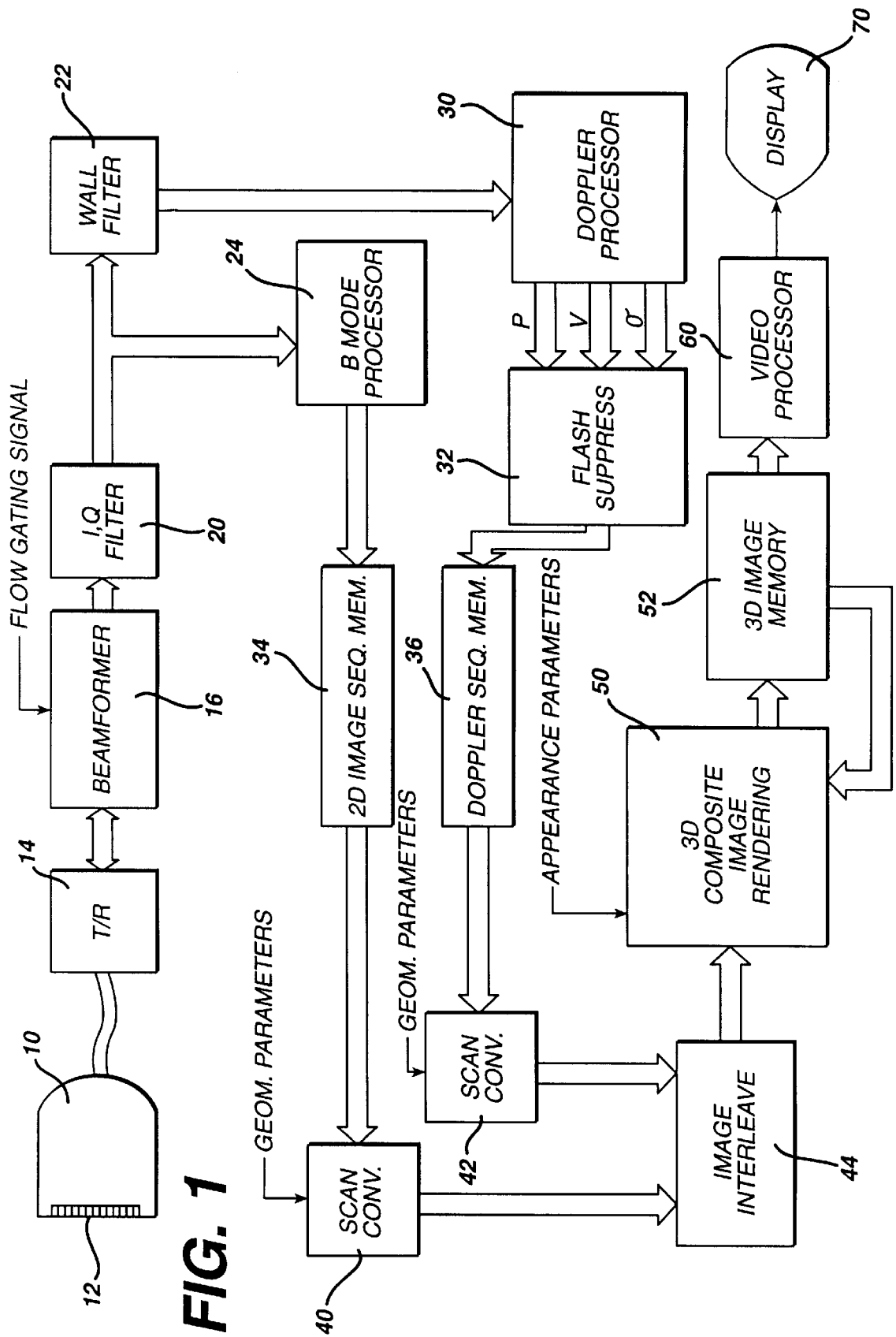
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A scanhead 10 includes a transducer array 12 which transmits ultrasonic pulses into a patient and receives ultrasonic echoes. The transducer array 12 is pulsed and echoes received by a transmitter/receiver 14. To scan a volumetric region which is to be displayed three dimensionally, the scanhead is swept over the region to acquire a sequence of planar 2D images which scan two dimensions of the volumetric region by their x,y dimensions, and the third dimension by the interplane spacing of the spatial image sequence. Ultrasonic beams transmitted and received by the transducer array are steered and focused under control of a beamformer 16, which processes echo signals from a plurality of elements to form scanlines of coherent echo signals. The received echo signals are quadrature detected and filtered by an I,Q filter 20, then processed for either B mode or Doppler display.

For B mode processing the I and Q samples are coupled to a B mode processor 24, which detects and maps the detected signals to produce grayscale signals with brightness corresponding to the intensity of echo signals returned from tissue. The grayscale signals are stored as groups of signals corresponding to a 2D B mode image frame in a 2D image sequence memory 34. The B mode image frames are stored in the memory 34 in the sequence in which they are received. In a preferred embodiment scanlines of grayscale signals are acquired to form a full planar image, and a sequence of B mode planar tissue images is stored in the 2D image sequence memory 34. The image planes retain their spatial orientation to each other by being stored in the time or spatial sequence in which they were acquired.

For Doppler processing the I and Q samples undergo highpass filtering in a wall filter 22, then are assembled in ensembles of Doppler data in a Doppler processor 30. The data ensembles are processed by a Doppler technique such as autocorrelation or Fourier transform processing to produce Doppler signals of flow characteristics such as Doppler power (P), velocity (v), or variance (σ). The Doppler signals are processed to remove motion artifacts in a flash suppresser 32, then stored in a Doppler image sequence memory 36. In a preferred embodiment scanline ensembles of Doppler signals are acquired to form a full planar image, and a sequence of Doppler images is stored in the Doppler image sequence memory, which may be a partition of the 2D image memory 34, or a separate memory. The Doppler images retain their spatial orientation to each other by being stored in the time or spatial sequence in which they were acquired. The tissue and Doppler images are separately scan converted into the desired image format, such as a sector format, by scan converters 40 and 42. Separate scan converters may be employed to rapidly scan convert tissue and Doppler images simultaneously, or a single scan converter may be used by time multiplexing the processing of the two types of image information. Scan conversion may also be merged into the rendering operation, whereby portions of the two functions are carried out together (i.e., convert polar coordinate scanlines directly into a rectilinearly addressed three dimensional projection.) In a preferred embodiment, the scan converters 40,42 perform the geometric portion of the 3D rendering by receiving geometric parameters and scan converting the images into the appropriate frame heights, widths and relative offsets as shown by FIGS. 3a–5d of my U.S. Pat. No. 5,485,842.

The separate B mode (tissue) and Doppler (blood flow) images are processed together in accordance with the principles of the present invention to render a composite three dimensional presentation. Both tissue and blood flow images are rendered together to produce a 3D image of composite pixels from the pixels of the overlaid 2D images which are encountered when vectors along a viewing direction are directed through the 2D images. This viewing vector processing is described in the aforementioned U.S. patent [application Ser. No. 08/638,710].

In accordance with the present invention, 2D and flow (or motion) images are alternately provided to a 3D composite image rendering processor 50 by an image interleave sequencer 44. By interleaving 2D and flow images from the two spatially ordered sequences the resultant 3D image will be correctly perceptually rendered, with tissue and blood vessels properly appearing in front of and behind other tissue and vessels, and correctly moving in front of and behind other tissue and vessels as the 3D view of the volume being rendered is changed. This is accomplished in accordance with the principles of the present invention without the use of a three dimensional memory or z-buffer. The rendering processor 50 implements various 3D appearance parameters such as variable opacity for tissue and blood flow and controllable brightness gradient from front to rear in the three dimensional presentation. In a constructed embodiment, the 2D and Doppler images are sequentially processed to assemble a 3D rendered image in an image area of 3D image memory 52. Partially rendered 3D images are transferred back to the rendering processor 50 from the 3D image memory 52, and the completed 3D image, completed when all of the sequential 2D and Doppler images have been combined, is stored in the 3D image memory. The next 3D image, at a different perspective view, is then rendered in another image area of the 3D image memory. Rendering is completed when a full set of 3D images, spanning the full range of desired viewing perspectives, has been completed and stored in the 3D image memory 52. The 3D image sequence may then be read out of the 3D image memory by a video processor 60 for display either statically or as a moving 3D presentation on a display 70.

Figure 2:
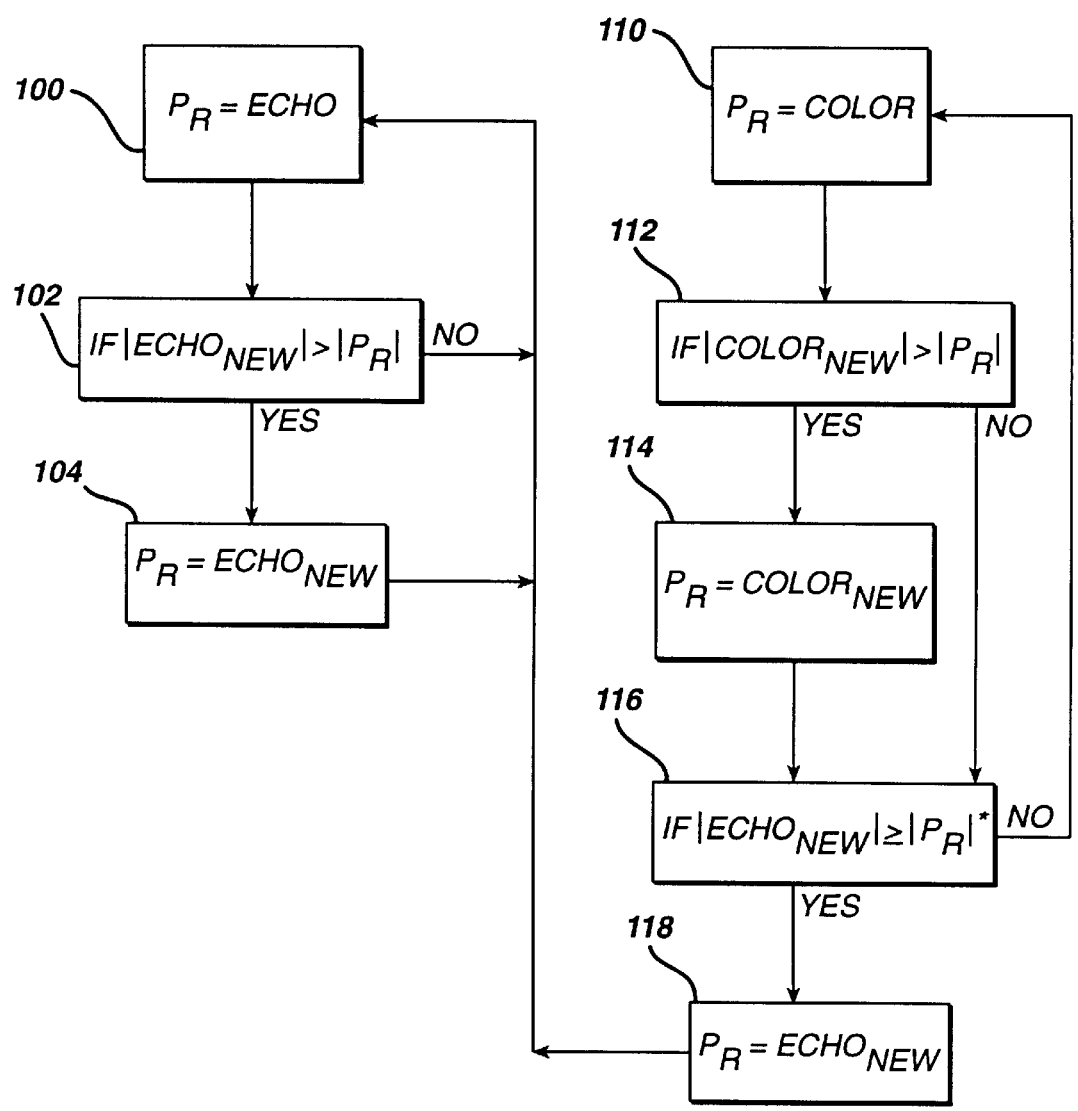
FIG. 2 illustrates in block diagram form a technique for rendering a three dimensional image of tissue and flow in which tissue is given preference.
Figure 3:
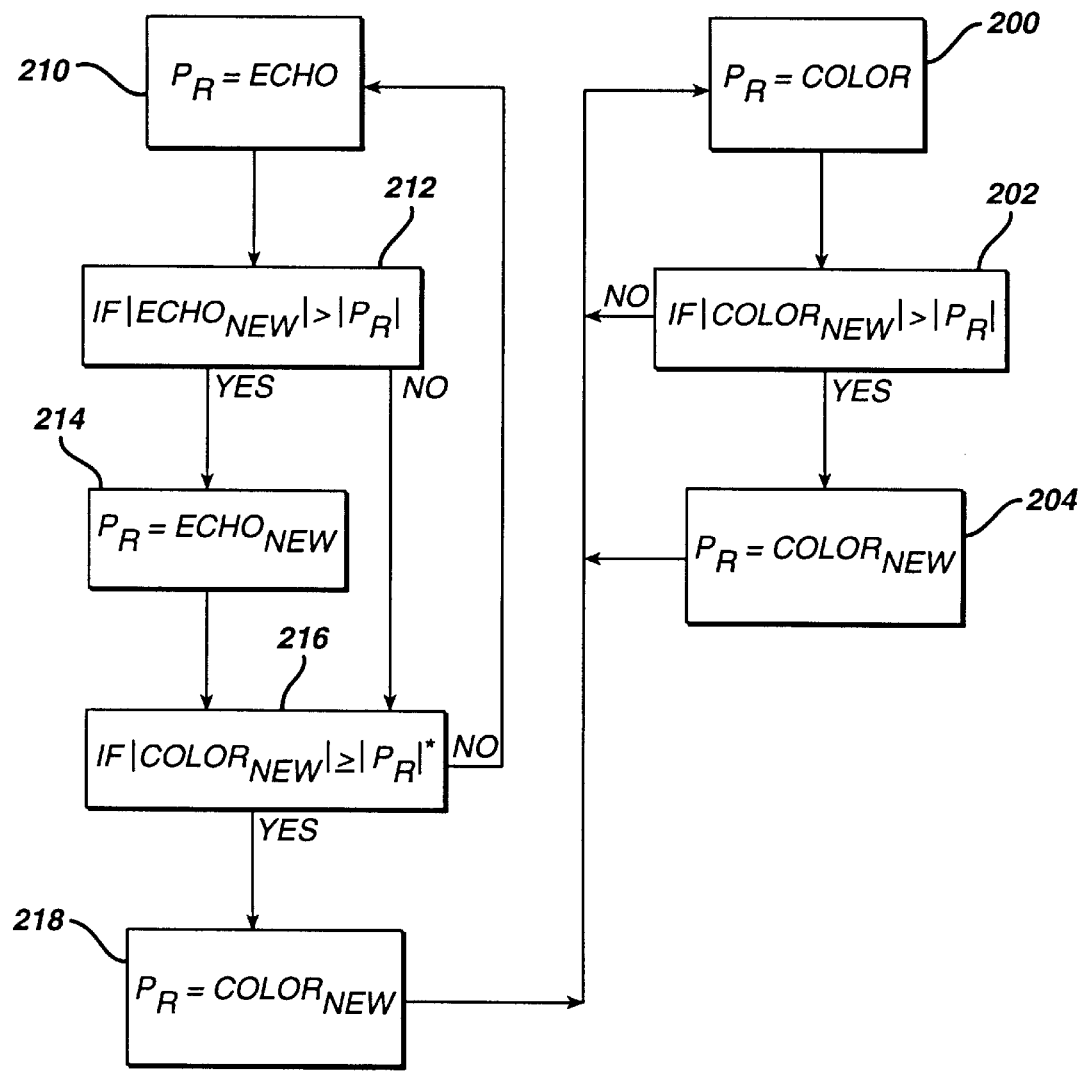
FIG. 3 illustrates in block diagram form a technique for rendering a three dimensional image of tissue and flow in which flow is given preference.
Figure 4:
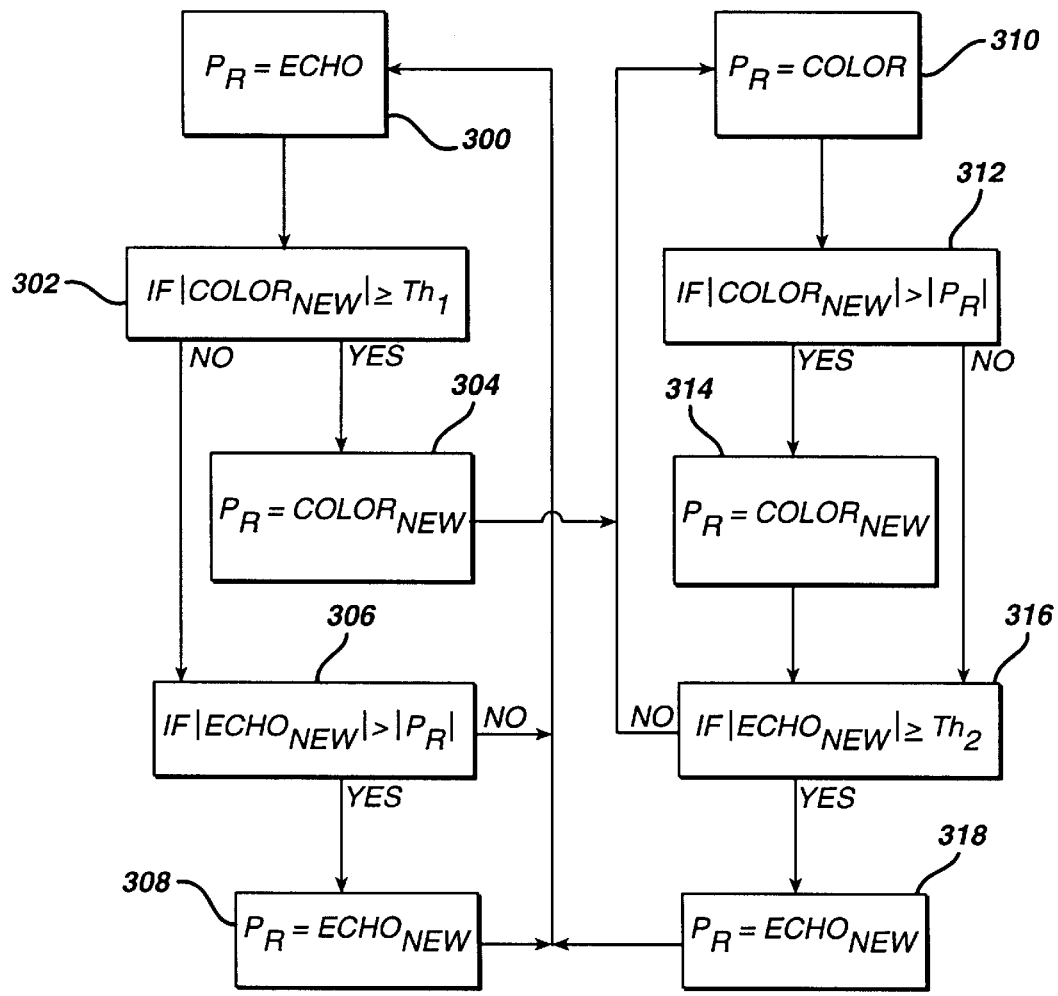
FIG. 4 illustrates in block diagram form a technique for rendering a three dimensional image of tissue and flow in which tissue and flow are blended together.

Three dimensional images are rendered in accordance with the present invention by one of the techniques shown in FIGS. 2–4. Referring first to FIG. 2, a rendering technique which give priority to tissue in the 3D image is shown. In FIGS. 2–4, "echo" refers to B mode (tissue) image elements (pixels) and "color" refers to flow (Doppler) image elements. $P_R$ refers to the rendered pixel of a 3D image which is formed from pixels of the interleaved and overlaid 2D and Doppler images. The flowcharts of these drawings start from two points, one where the 3D pixel $P_R$ is initially an echo pixel, and another where the 3D pixel $P_R$ is initially a color pixel.

In the rendering process of FIG. 2, in which echo pixels are given priority, a color pixel will never replace an echo pixel. Thus, when the rendered pixel $P_R$ is initially an echo pixel (box 100), it is only necessary to compare the absolute value of the pixel of the next 2D image frame, $Echo_{New}$, to the absolute value of the current 3D pixel $P_R$ (box 102), and update the 3D pixel $P_R$ to the new echo value if the new echo value exceeds the value of the current 3D pixel $P_R$ (box 104). The process is then ready to process the next pair of 2D and Doppler images.

If the current 3D pixel $P_R$ is a color pixel (box 110), the process begins by comparing the pixel of the next Doppler frame, $Color_{New}$, with the color $P_R$ pixel (box 112). If the value of the new pixel exceeds that of the 3D pixel, the 3D pixel is updated to the value of the new color pixel (box 114). Otherwise, the process continues with the current 3D pixel value. The pixel of the next 2D image, $Echo_{New}$, is compared with the value of the 3D color pixel $P_R$ (box 116). If the new echo value is greater than or equal to the value of the color pixel, the color pixel is set to the new echo value (box 118). If it is not, the 3D color pixel $P_R$ remains unchanged.

As an alternative to comparing the new echo value with the 3D pixel, the new echo value can be compared with a chosen threshold value Th, as indicated by the asterisk in box 116. Echo values exceeding the threshold are used as the new (echo) value for the 3D pixel $P_R$.

Processing continues with interleaved 2D and Doppler images being submitted by the image interleave sequencer for processing until all of the 2D and Doppler images have been processed to render a 3D image. Rendering can be done view vector by view vector, but is preferably done frame by frame, with each pixel in an image being processed before turning to the next image.

FIG. 3 illustrates a rendering process in which flow pixels take priority, and is a mirror of the process of FIG. 2. Since an echo pixel will never replace a color pixel as the 3D pixel, if the 3D pixel is initially a color pixel (box 200), a comparison is made to see if the 3D pixel should be updated to the value of a new color pixel. A comparison of the absolute value of the color pixel of a new Doppler image, $Color_{New}$, with the 3D color pixel $P_R$ (box 202) is made, and if the new pixel value is greater the 3D pixel is updated to the new color pixel value (box 204). Otherwise, the 3D pixel is unchanged ("No" decision from box 202).

If the current 3D rendered pixel $P_R$ is an echo pixel (box 210), the pixel of the new 2D image, $Echo_{New}$, is compared to the 3D pixel (box 212). If the new echo value exceeds that of the 3D pixel, the rendered pixel is updated to the new echo value (box 214). The current or updated 3D pixel value, as the case may be, is then compared with the pixel value at that location in the new Doppler image, $Color_{New}$ (box 216). If the new color value is equal or greater than the 3D echo value, the new color value $Color_{New}$ is used as the 3D pixel value (box 218). Otherwise, the current value for $P_R$ remains unchanged ("No" line out of box 216).

As in the previous process, as an alternative to comparing the new color value with the 3D pixel in box 216, the new color value can be compared with a chosen threshold value Th, as indicated by the asterisk in box 216. Color values exceeding the threshold are used as the new (color) value for the 3D pixel $P_R$.

FIG. 4 illustrates a rendering process in which color and echo pixels are blended together. Blending means, for instance, that the blended pixel can have the hue or shade of a color pixel and the maximum or average of the brightness of two pixels. If the 3D pixel is initially an echo pixel (box 300), the process begins by comparing the absolute value of the new color pixel of the next Doppler image, $Color_{New}$, with a first threshold value $Th_1$ (box 302). If the new color pixel is greater than or equal to the value of the threshold, the 3D pixel is changed to the new color pixel (box 304). Next, the absolute value of the new echo pixel of the next 2D image, $Echo_{New}$, is compared with the absolute value of the 3D pixel (box 306). If the new echo pixel is greater, the 3D pixel is changed to the new echo pixel (box 308). If not, there is no subsequent change to the 3D pixel and the process moves to the next 2D and Doppler images.

If the 3D pixel is initially a color pixel (box 310), the process begins by comparing the absolute value of the new color pixel of the next Doppler image, $Color_{New}$, with the 3D pixel value $P_R$ (box 312). If the new color pixel value is greater than or equal to the value of the 3D pixel, the 3D pixel is changed to the new color pixel (box 314). Next, the absolute value of the new echo pixel of the next 2D image, $Echo_{New}$, is compared to a second threshold value $Th_2$ (box 316). If the new echo pixel value is greater than or equal to the $Th_2$ threshold, the 3D pixel is changed to the new echo pixel (box 318). If not, there is no subsequent change to the 3D pixel and the process moves to the next 2D and Doppler images.

The color priority and blending techniques present perceptionally accurate three dimensional views which avoid potential problems such as near field tissue echoes suddenly obscuring flow which passes to the rear or tissue echoes suddenly disappearing when moving in front of flow in the far field as the three dimensional presentation is rotated in space. Perceptionally accurate image may be rendered by processing the 2D and Doppler images in either a front to rear sequence or a rear to front sequence.

The flowcharts of FIGS. 2–4 illustrate maximum intensity renderings, where the maximum of the current or new value is used. It will be appreciated that renderings other than maxim intensity may be performed with these flowcharts, for instance, by using an average or weighted average of old and new values to replace a current rendered value. Typical formulas for weighted averaging are $$P_{R(new)} = aP_{R(Old)} + bColor_{New}$$ or $$P_{R(new)} = aP_{R(Old)} + bEcho_{New}$$

where a and b are weighting coefficients.

It will also be appreciated that a scaling or remapping or other rationalization may be needed to compare color and echo values. For example if echo values have more digital bits than color values, the two will need to be equated to a common basis before making the comparisons of these flowcharts. Scaling of the 2D and Doppler values can efficiently be performed by a look-up table for each image type, and the scaling can effect other mapping effects such as log compression of the signal dynamic range. The scaling can also effect some three dimensional appearance effects. For example, scaling of the tissue pixels to a new range can effect a transparency effect to the tissue as described in the aforementioned U.S. patent [application Ser. No. 08/638, 710] through a reweighting of tissue values.

It will further be appreciated that it may be more efficient for the image interleave sequencer 44 to present the interleaved tissue and flow images for 3D rendering in a certain order. For example, the echo priority rendering of FIG. 2 will operate more efficiently by operating on the color image before the echo image from a given location. The color priority technique of FIG. 3 will operate more efficiently by considering the echo image first. The blending technique will be equally efficient by considering either image first.

Modifications to the interleave sequence are within the scope of the present invention. For instance, correct spatial relations may still be maintained by operating on two consecutive echo frames, then two consecutive color frames in an alternating sequence.

The present three dimensional display technique can be performed with any type of Doppler flow information, such as power Doppler or velocity (color flow) information. While the ultrasonic Doppler and B mode echo information can be obtained by gating the acquisition of both types of information to a phase of the pulsatile flow of blood, it has been found that excellent three dimensional renderings of pulsatile structures may be obtained by utilizing ungated power Doppler signal acquisition and gated B mode acquisition. Essentially, power Doppler information is acquired as rapidly and often as possible, while tissue information is acquired only at the desired phase of the heart cycle. After the power Doppler information has been temporally averaged, a combined rendering of tissue and blood flow information displays the blood flow information in spatial correspondence with the tissue structure.

What is claimed is:

1. A medical diagnostic ultrasound system which develops three dimensional images of flow or motion and structure in a volumetric region of the body comprising:

an ultrasonic transducer for receiving ultrasonic echoes;

a tissue image processor for processing ultrasonic echoes to produce tissue display information;

a flow and motion image processor for processing ultrasonic echoes to produce or motion flow display information; and a three dimensional image processor for processing said tissue and said flow or motion display information in an interleaved sequence to form a three dimensional image.

2. The medical diagnostic ultrasound system of claim 1, wherein said tissue image processor and said flow and motion image processor acquire a tissue image and a flow or motion image in rapid succession to produce a tissue and flow or motion image pair from substantially the same time interval;

wherein said three dimensional image processor processes a sequence of flow or motion images, and a sequence of tissue images which is paired with said sequence of flow or motion images.

3. The medical diagnostic ultrasound system of claim 2, further comprising a first storage area for storing said sequence of tissue images; and a second storage area for storing said sequence of flow or motion images; and an image interleave sequencer for presenting tissue and flow or motion images to said three dimensional image processor in an interleaved sequence.

4. The medical diagnostic ultrasound system of claim 1, wherein said tissue image processor comprises means for producing a sequence of spatially discrete planar tissue images from said volumetric region;

wherein said flow and motion image processor comprises means for producing a sequence of spatially discrete planar flow or motion images from said volumetric region, ones of which correspond spatially to ones of said planar tissue images; and wherein said three dimensional image processor comprises means for processing said planar tissue and flow or motion images in an interleaved sequence to render a three dimensional image of tissue and flow or motion.

5. The medical diagnostic ultrasound system of claim 4, further comprising a first memory area for storing said sequence of planar tissue images; and a second memory area for storing said sequence of planar flow or motion images; and means for presenting said tissue and flow or motion images to said three dimensional image processor in an interleaved sequence.

6. A method for rendering a three dimensional ultrasonic image pixel from a plurality of overlapping ultrasonic two dimensional image pixels of tissue and flow comprising the steps of:

a) comparing a partially rendered three dimensional ultrasonic tissue image pixel with one of said two dimensional tissue image pixels, and setting the value of said partially rendered three dimensional ultrasonic tissue image pixel on the basis of said comparison; or b) comparing a partially rendered three dimensional ultrasonic flow image pixel with one of said two dimensional flow image pixels, and setting the value of said partially rendered three dimensional ultrasonic flow image pixel on the basis of said comparison; and c) comparing a partially rendered three dimensional ultrasonic flow image pixel with one of said two dimensional tissue image pixels, and setting the value of said partially rendered three dimensional ultrasonic image pixel on the basis of said comparison.

7. The method of claim 6, wherein step c) comprises the step of:

c) comparing a threshold value with one of said two dimensional tissue image pixels, and setting the value of said partially rendered three dimensional ultrasonic image pixel on the basis of said comparison.

8. A method for rendering a three dimensional ultrasonic image pixel from a plurality of overlapping ultrasonic two dimensional image pixels of tissue and flow comprising the steps of:

a) comparing a partially rendered three dimensional ultrasonic flow image pixel with one of said two dimensional flow image pixels, and setting the value of said partially rendered three dimensional ultrasonic flow image pixel on the basis of said comparison; or b) comparing a partially rendered three dimensional ultrasonic tissue image pixel with one of said two dimensional tissue image pixels, and setting the value of said partially rendered three dimensional ultrasonic tissue image pixel on the basis of said comparison; and c) comparing a partially rendered three dimensional ultrasonic tissue image pixel with one of said two dimensional flow image pixels, and setting the value of said partially rendered three dimensional ultrasonic image pixel on the basis of said comparison.

9. The method of claim 8, wherein step c) comprises the step of:

c) comparing a threshold value with one of said two dimensional flow image pixels, and setting the value of said partially rendered three dimensional ultrasonic image pixel on the basis of said comparison.

10. A method for rendering a three dimensional ultrasonic image pixel from a plurality of overlapping ultrasonic two dimensional image pixels of tissue and flow comprising the steps of:

a) comparing a two dimensional flow image pixel with a threshold value and setting the value of said partially rendered three dimensional ultrasonic image pixel on the basis of said comparison; and b) comparing a two dimensional tissue image pixel with said partially rendered three dimensional ultrasonic image pixel and setting the value of said partially rendered three dimensional ultrasonic image pixel on the basis of said comparison; or c) comparing a partially rendered three dimensional ultrasonic image pixel with a two dimensional flow image pixel and setting the value of said partially rendered three dimensional ultrasonic image pixel on the basis of said comparison; and d) comparing a two dimensional tissue image pixel with a threshold value and setting the value of said partially rendered three dimensional ultrasonic image pixel on the basis of said comparison.

* * * * *